US012751732B2

(12) United States Patent
Aibe et al.

(10) Patent No.: US 12,751,732 B2
(45) Date of Patent: Oct. 6, 2026

(54) SURGICAL MEDICAL INSTRUMENT AND GRIPPING DEVICE

(71) Applicant: KAWASAKI JUKOGYO KABUSHIKI KAISHA, Kobe (JP)

(72) Inventors: Toru Aibe, Kobe (JP); Takeshi Matsuura, Kobe (JP); Tamami Oryu, Kobe (JP); Eiji Sato, Kobe (JP); Yohei Murase, Kobe (JP)

(73) Assignee: KAWASAKI JUKOGYO KABUSHIKI KAISHA, Kobe (JP)

( * ) Notice: Subject to any disclaimer, the term of this patent is extended or adjusted under 35 U.S.C. 154(b) by 159 days.

(21) Appl. No.: 18/712,151

(22) PCT Filed: Oct. 26, 2022

(86) PCT No.: PCT/JP2022/039862

§ 371 (c)(1),
(2) Date: May 21, 2024

(87) PCT Pub. No.: WO2023/105967

PCT Pub. Date: Jun. 15, 2023

(65) Prior Publication Data

US 2025/0017610 A1 Jan. 16, 2025

(30) Foreign Application Priority Data

Dec. 7, 2021 (JP) ................................ 2021-198307

(51) Int. Cl.
*A61B 17/29* (2006.01)
*A61B 17/00* (2006.01)

(52) U.S. Cl.
CPC .... *A61B 17/29* (2013.01); *A61B 2017/00477* (2013.01); *A61B 2017/00539* (2013.01); *A61B 2017/2929* (2013.01); *A61B 2017/2946* (2013.01)

(58) Field of Classification Search
CPC .......... A61B 17/29; A61B 2017/00477; A61B 2017/00539; A61B 2017/2929; A61B 2017/2938; A61B 2017/2939; A61B 2017/294; A61B 34/30
See application file for complete search history.

(56) References Cited

FOREIGN PATENT DOCUMENTS

| | | | | |
|---|---|---|---|---|
| DE | 102014204568 A1 * | 9/2015 | | A61B 34/30 |
| DE | 102015204486 A1 | 9/2016 | | |
| DE | 102013211698 B4 | 7/2017 | | |
| DE | 102014204568 B4 | 5/2019 | | |
| WO | 2016/129526 A1 | 8/2016 | | |

* cited by examiner

*Primary Examiner* — Brooke Labranche
(74) *Attorney, Agent, or Firm* — Oliff PLC

(57) ABSTRACT

A surgical medical instrument (100) includes a first jaw (11) and a second jaw (12) operable to be rotated about a jaw rotation axis (A1) and about a wrist rotation axis (A2) by a first piston (31), a second piston (32), a third piston (33), and a fourth piston (34).

15 Claims, 14 Drawing Sheets

SURGICAL MEDICAL INSTRUMENT AND GRIPPING DEVICE

TECHNICAL FIELD

The present disclosure relates to a surgical medical instrument and a gripping device.

BACKGROUND ART

Conventionally, a surgical medical instrument including a pair of jaws is known. For example, German Patent Application Publication No. 102014204568 discloses a surgical medical instrument including a pair of jaws, four hydraulic cylinders that rotate the pair of jaws about a jaw rotation axis, and two hydraulic cylinders that rotate the pair of jaws about a wrist rotation axis. In German Patent Application Publication No. 102014204568, the four hydraulic cylinders that rotate the jaws about the jaw rotation axis and the two hydraulic cylinders that rotate the jaws about the wrist rotation axis are placed in series along the longitudinal direction of the surgical medical instrument. Furthermore, in German Patent Application Publication No. 102014204568, the surgical medical instrument curves or bends to pass around an obstacle within the body of a patient.

PRIOR ART

Patent Document

Patent Document 1: German Patent Application Publication No. 102014204568

SUMMARY OF THE INVENTION

In the surgical medical instrument disclosed in German Patent Application Publication No. 102014204568, the four hydraulic cylinders that rotate the jaws about the jaw rotation axis and the two hydraulic cylinders that rotate the jaws about the wrist rotation axis are placed in series along the longitudinal direction of the surgical medical instrument, and thus the length of the surgical medical instrument becomes relatively large. Therefore, when the surgical medical instrument curves or bends to pass around an obstacle within the body of the patient, it becomes difficult for the surgical medical instrument to enter a narrow space within the body of the patient. Thus, when the length of the surgical medical instrument is relatively large, a problem may occur, and it is desired to reduce the length of the surgical medical instrument.

The present disclosure is intended to solve the above problem. The present disclosure aims to provide a surgical medical instrument and a gripping device that each allow the length of the surgical medical instrument to be reduced.

A surgical medical instrument according to a first aspect of the present disclosure includes a first jaw, a second jaw, a first piston and a second piston to rotate the first jaw, a third piston and a fourth piston to rotate the second jaw, a first link to connect the first jaw to the first piston, a second link to connect the first jaw to the second piston, a third link to connect the second jaw to the third piston, and a fourth link to connect the second jaw to the fourth piston. The first to fourth pistons are placed in parallel in a direction intersecting with a longitudinal direction of the surgical medical instrument, and the first jaw and the second jaw are operable to be rotated about a jaw rotation axis and about a wrist rotation axis by the first to fourth pistons.

In the surgical medical instrument according to the first aspect of the present disclosure, as described above, the first jaw and the second jaw are operable to be rotated about the jaw rotation axis and about the wrist rotation axis by the four pistons. Furthermore, the four pistons are placed in parallel in the direction intersecting with the longitudinal direction of the surgical medical instrument. Accordingly, as compared with a case in which pistons for rotating the first jaw and the second jaw about the jaw rotation axis and pistons for rotating the first jaw and the second jaw about the wrist rotation axis are placed separately, and the pistons for rotating the first jaw and the second jaw about the jaw rotation axis and the pistons for rotating the first jaw and the second jaw about the wrist rotation axis are placed in series along the longitudinal direction of the surgical medical instrument, the length of the surgical medical instrument can be reduced. Therefore, when the surgical medical instrument curves or bends to pass around an obstacle within the body of a patient, the surgical medical instrument can easily enter a narrow space.

A gripping device according to a second aspect of the present disclosure includes a first gripper, a second gripper, a first piston and a second piston to rotate the first gripper, a third piston and a fourth piston to rotate the second gripper, a first link to connect the first gripper to the first piston, a second link to connect the first gripper to the second piston, a third link to connect the second gripper to the third piston, and a fourth link to connect the second gripper to the fourth piston. The first to fourth pistons are placed in parallel in a direction intersecting with a longitudinal direction of the gripping device, and the first gripper and the second gripper are operable to be rotated about a gripper rotation axis and about a wrist rotation axis by the first to fourth pistons.

In the gripping device according to the second aspect of the present disclosure, as described above, the first gripper and the second gripper are operable to be rotated about the gripper rotation axis and about the wrist rotation axis by the four pistons. Furthermore, the four pistons are placed in parallel in the direction intersecting with the longitudinal direction of the gripping device. Accordingly, as compared with a case in which pistons for rotating the first gripper and the second gripper about the gripper rotation axis and pistons for rotating the first gripper and the second gripper about the wrist rotation axis are placed in series along the longitudinal direction of the gripping device, the length of the gripping device can be reduced. Therefore, when the gripping device curves or bends to pass around an obstacle, the gripping device can easily enter a narrow space.

According to the present disclosure, it is possible to reduce the lengths of the surgical medical instrument and the gripping device.

MODES FOR CARRYING OUT THE INVENTION

First Embodiment

Figure 1:
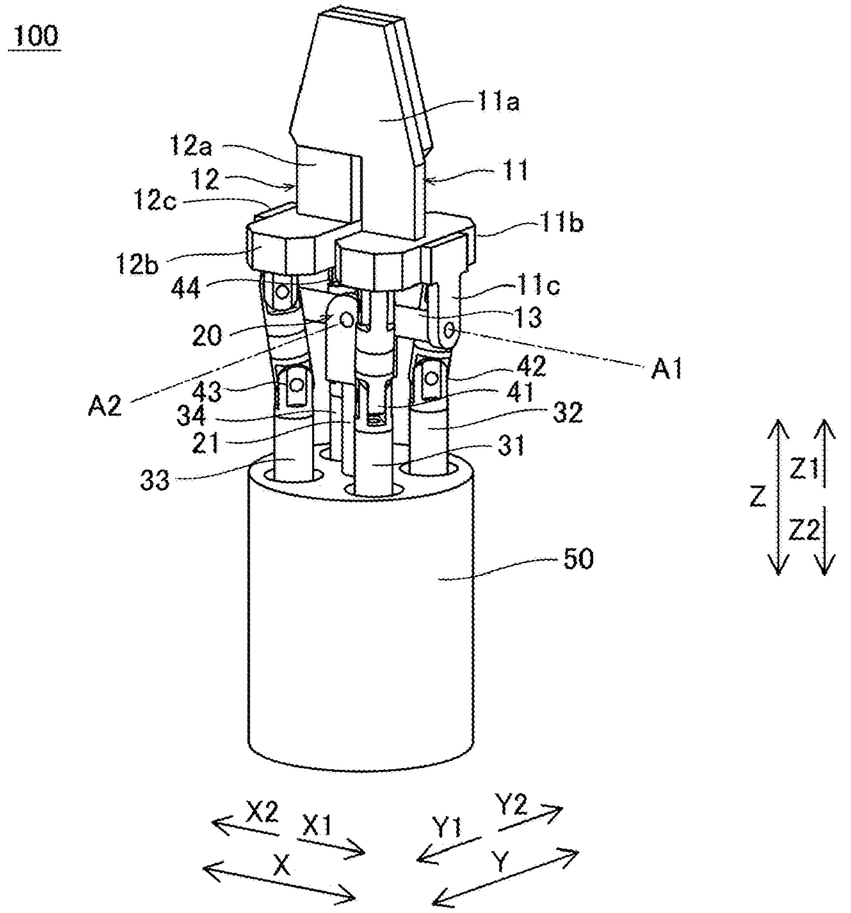
FIG. 1 is a perspective view of a surgical medical instrument according to a first embodiment.
Figure 2:
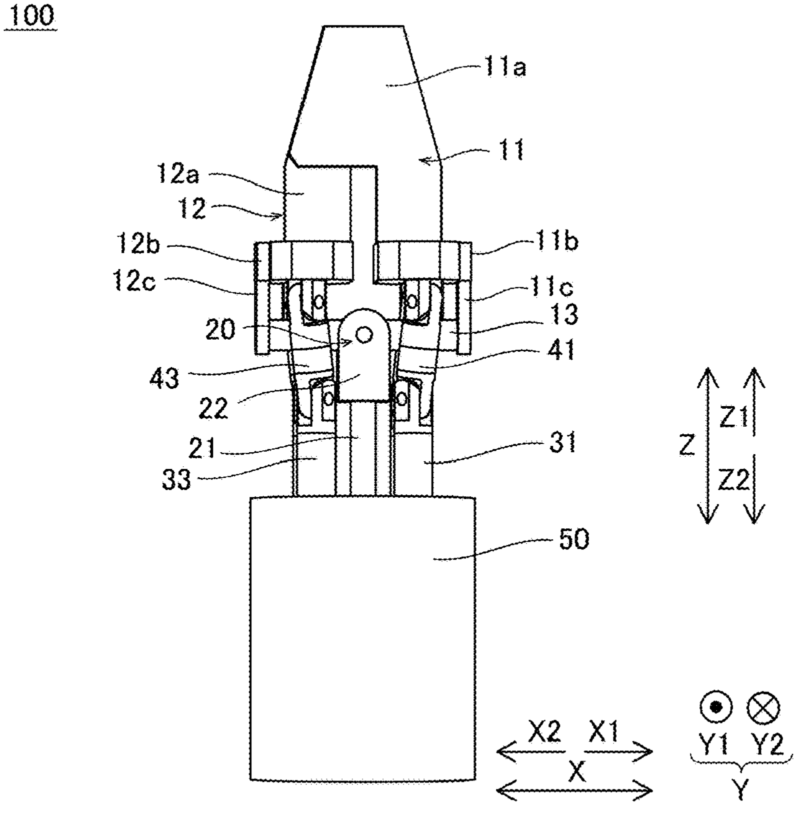
FIG. 2 is a side view of the surgical medical instrument according to the first embodiment.
Figure 4:
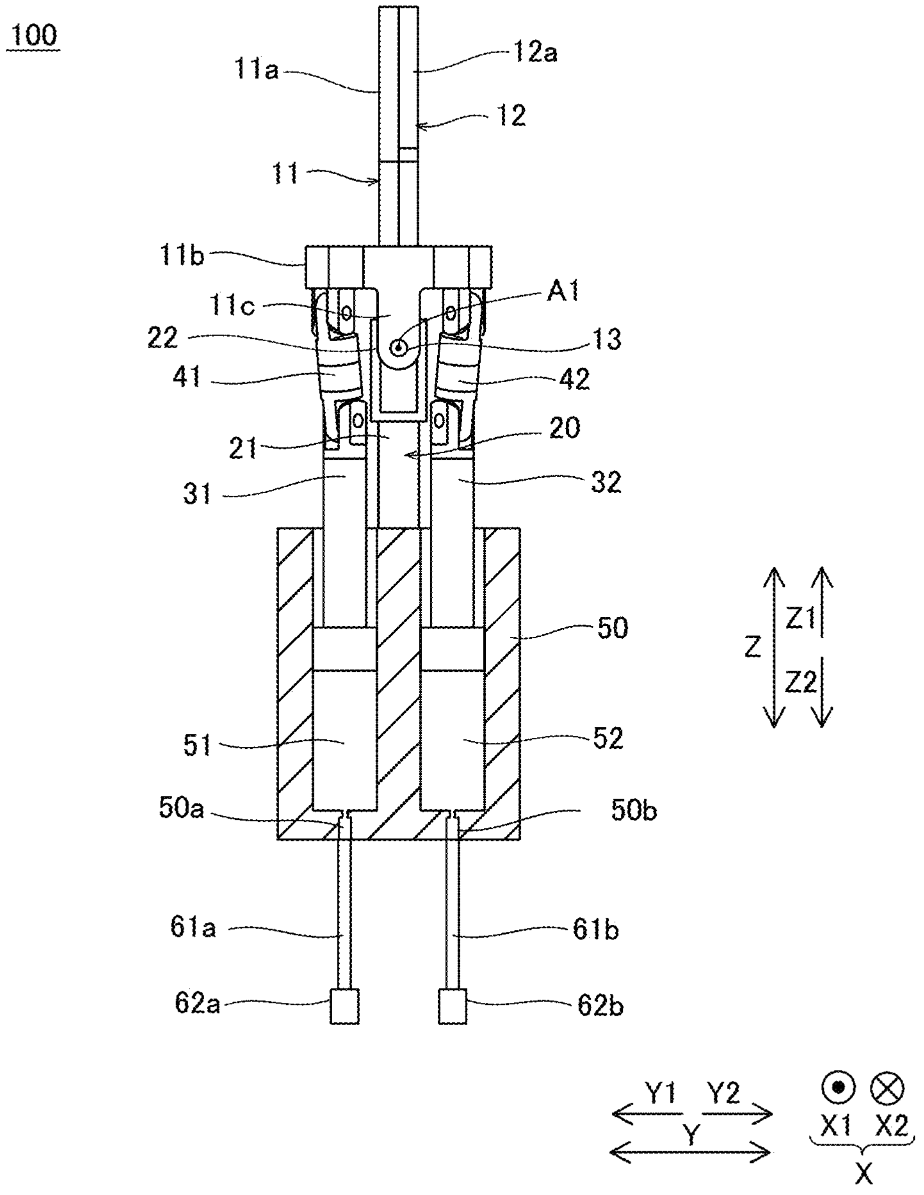
FIG. 4 is a sectional view of the surgical medical instrument according to the first embodiment, as viewed from an X1 side.
Figure 5:
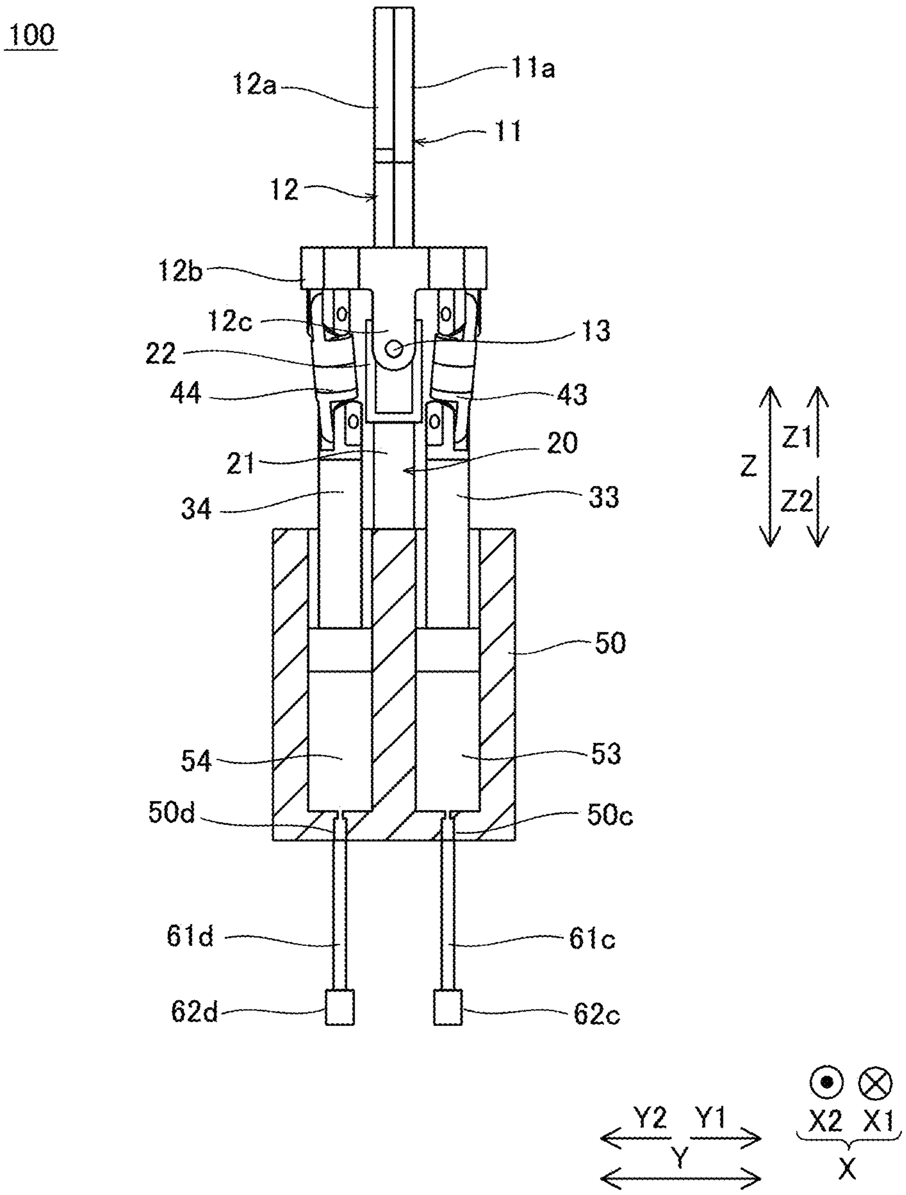
FIG. 5 is a sectional view of the surgical medical instrument according to the first embodiment, as viewed from an X2 side.

The configuration of a surgical medical instrument 100 according to a first embodiment is now described with reference to FIGS. 1 to 8. In the first embodiment, the surgical medical instrument 100 is a pair of forceps driven by a fluid pressure. As shown in FIG. 1, the surgical medical instrument 100 includes a first jaw 11, a second jaw 12, a shaft 13, a support 20, four links 41, 42, 43, and 44, and a cylinder main body 50. As shown in FIG. 4, the surgical medical instrument 100 includes a first piston 31, a second piston 32, a first fluid drive 62*a*, and a second fluid drive 62*b*. As shown in FIG. 5, the surgical medical instrument 100 includes a third piston 33, a fourth piston 34, a third fluid drive 62*c*, and a fourth fluid drive 62*d*. In the surgical medical instrument 100, the first jaw 11 and the second jaw 12 are rotated about a jaw rotation axis A1 and a wrist rotation axis A2.

In this description, the longitudinal direction of the surgical medical instrument 100 is defined as a Z direction. The distal end side of the surgical medical instrument 100 is defined as a Z1 side, and the proximal end side of the surgical medical instrument 100 is defined as a Z2 side. A direction perpendicular to the Z direction is defined as an X direction. One side in the X direction is defined as an X1 side, and the other side is defined as an X2 side. A direction perpendicular to the Z direction and the X direction is defined as a Y direction. One side in the Y direction is defined as a Y1 side, and the other side is defined as a Y2 side.

Figure 3:
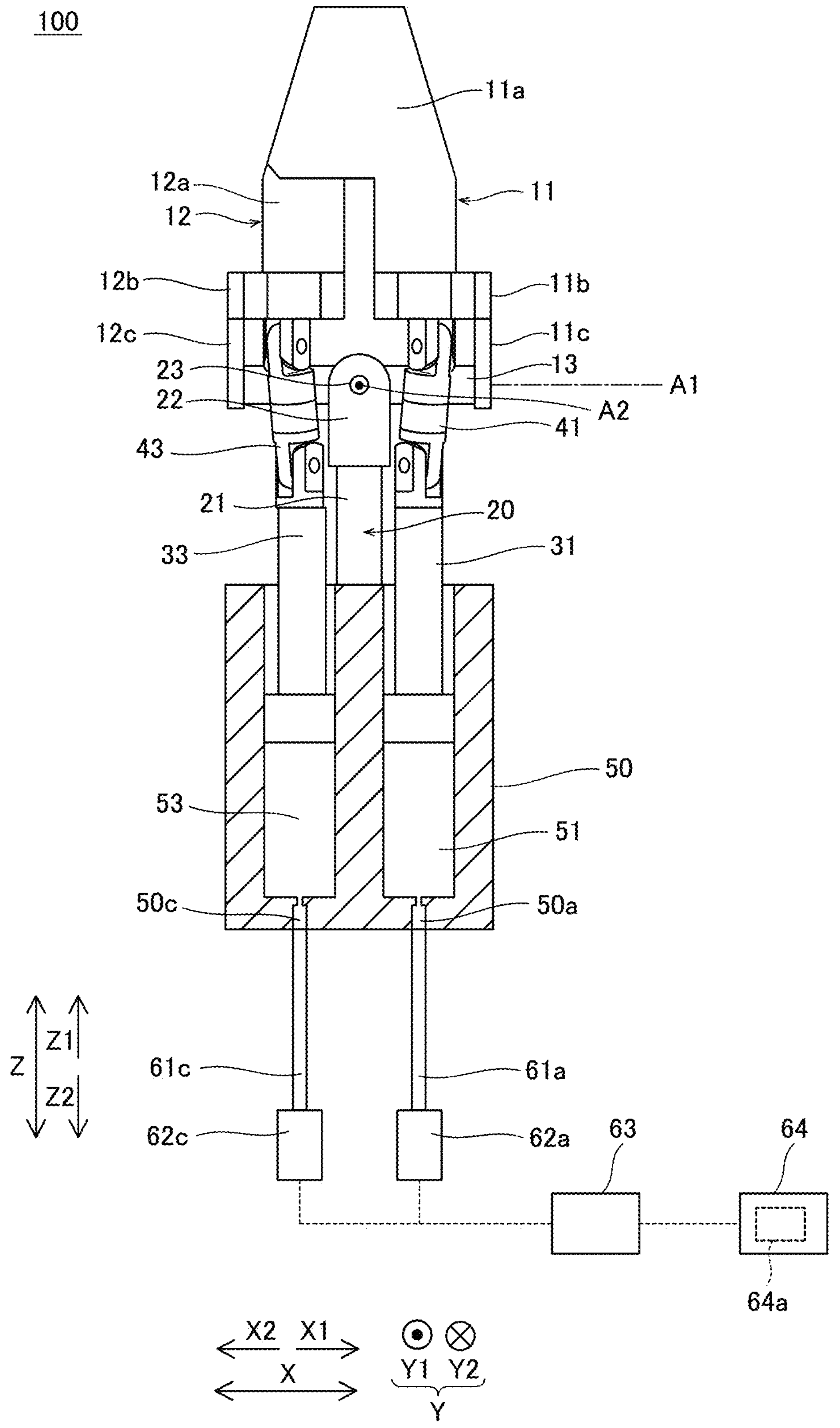
FIG. 3 is a sectional view of the surgical medical instrument according to the first embodiment, as viewed from a Y1 side.

As shown in FIG. 3, the first jaw 11 includes a distal end 11*a*, a proximal end 11*b* that supports the distal end 11*a*, and a connector 11*c* connected to the shaft 13. The second jaw 12 includes a distal end 12*a*, a proximal end 12*b* that supports the distal end 12*a*, and a connector 12*c* connected to the shaft 13. The distal end 11*a*, the proximal end 11*b*, and the connector 11*c* may be integral and unitary with or separate from each other. The distal end 12*a*, the proximal end 12*b*, and the connector 12*c* may be integral and unitary with or separate from each other.

In the first embodiment, the shaft 13 supports the first jaw 11 and the second jaw 12 and has the jaw rotation axis A1 and the wrist rotation axis A2. Specifically, the connector 11*c* of the first jaw 11 is connected to a first end of the shaft 13. The connector 12*c* of the second jaw 12 is connected to a second end of the shaft 13. The first jaw 11 and the second jaw 12 rotate about a central axis along the Z direction, which is the longitudinal direction of the shaft 13, as the jaw rotation axis A1. The first jaw 11 and the second jaw 12 rotate about the wrist rotation axis A2 perpendicular to the shaft 13. The jaw rotation axis A1 is along the X direction perpendicular to the Z direction, which is the longitudinal direction of the surgical medical instrument 100. The wrist rotation axis A2 is along the Y direction perpendicular to the Z direction.

The support 20 supports the shaft 13 such that the shaft 13 is rotatable. The shaft 13 supports the first jaw 11 and the second jaw 12. Specifically, the support 20 has a cylindrical column 21. A U-shaped member 22 is arranged at a distal end of the column 21. The shaft 13 that supports the first jaw 11 and the second jaw 12 passes through the U-shape of the member 22. Furthermore, a cylindrical pin member 23 passes through the U-shape of the members 22, and the pin member 23 passes through a central portion of the shaft 13. Thus, the shaft 13 rotates about the wrist rotation axis A2 using the pin member 23 as a rotation axis.

In the first embodiment, the shaft 13 is arranged between distal and proximal ends of each of the links 41, 42, 43, and 44 when the first jaw 11 and the second jaw 12 are arranged along the Z direction. The expression "when the first jaw 11 and the second jaw 12 are arranged along the Z direction" indicates "when the shaft 13 is arranged along the X direction". The distal end refers to an end of each of the links 41, 42, 43, and 44 on the Z1 side. The proximal end refers to an end of each of the links 41, 42, 43, and 44 on the Z2 side.

A proximal end of the support 20 is fixed to the cylinder main body 50. Specifically, the proximal end of the support 20 is fixed to the center of a surface of the cylinder main body 50 on the distal end side.

In the first embodiment, as shown in FIG. 4, the first link 41 connects the first jaw 11 to the first piston 31. The second link 42 connects the first jaw 11 to the second piston 32. As shown in FIG. 5, the third link 43 connects the second jaw 12 to the third piston 33. The fourth link 44 connects the second jaw 12 to the fourth piston 34.

Specifically, the first link 41 and the second link 42 are connected to the proximal end 11*b* of the first jaw 11. The third link 43 and the fourth link 44 are connected to the proximal end 12*b* of the second jaw 12.

Figure 6:
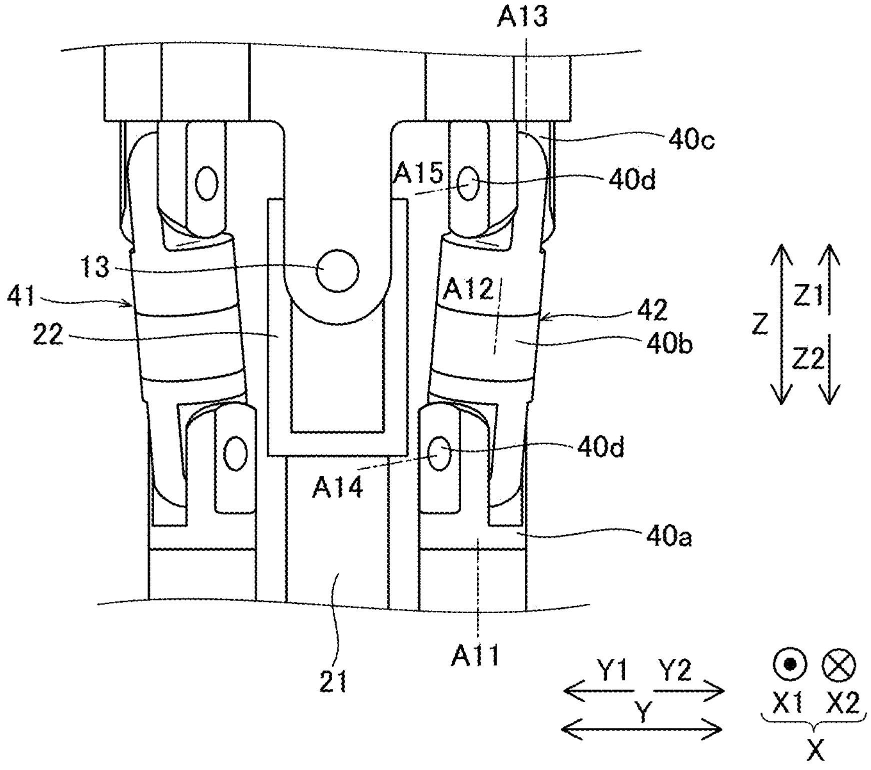
FIG. 6 is a partial enlarged view of the surgical medical instrument according to the first embodiment.

In the first embodiment, as shown in FIG. 6, the first link 41 and the second link 42 each have a plurality of rotational joints. Similarly, the third link 43 and the fourth link 44 each have a plurality of rotational joints. Specifically, each of the links 41, 42, 43, and 44 includes a first portion 40*a* on the proximal end side, a second portion 40*c* on the distal end side, and a third portion 40*b* located between the first portion 40*a* and the second portion 40*c*. A portion in which the first portion 40*a* is connected to the third portion 40*b* has a hinge structure and is bent about an axis A14. A portion in which the third portion 40*b* is connected to the second portion 40*c* has a hinge structure and is bent about an axis A15. The first portion 40*a*, the second portion 40*c*, and the third portion 40*b* each have a swivel structure. The links 41, 42, 43, and 44 each have five rotational degrees of freedom. The first portion 40*a* rotates about a direction of an axis A11, which is the longitudinal direction of the first portion 40*a*. The third portion 40*b* rotates about a direction of an axis A12, which is the longitudinal direction of the third portion 40*b*. The second portion 40*c* rotates about a direction of an axis A13, which is the longitudinal direction of the second portion 40*c*.

Specifically, the distal end side of the second portion 40*c* is connected to the proximal end 11*b* of the first jaw 11 or the proximal end 12*b* of the second jaw 12 so as to be rotatable about the axis A13. The distal end side of the third portion 40*b* is connected to the proximal end side of the second portion 40*c* so as to be rotatable about the axis A15. The proximal end side of the second portion 40*c* and the distal end side of the third portion 40*b* are fixed by pin members 40*d*. The proximal end side of the third portion 40*b* is connected to the distal end side of the first portion 40*a* so as to be rotatable about the axis A14. The distal end side of the first portion 40*a* and the proximal end side of the third portion 40*b* are connected to each other by the pin member 40*d*, and are freely rotatable about the pin member 40*d*. The proximal end side of the first portion 40*a* is connected to the distal end side of the first piston 31, the second piston 32, the third piston 33, or the fourth piston 34 so as to be rotatable about the axis A11. When the first jaw 11 and the second jaw 12 are arranged along the Z direction, the first portion 40*a*, the second portion 40*c*, and the third portion 40*b* are not arranged linearly.

In the first embodiment, as shown in FIGS. 4 and 5, the pistons 31, 32, 33, and 34 are placed in parallel in a direction intersecting with the Z direction. Specifically, the pistons 31, 32, 33, and 34 are housed in the cylinder main body 50. The pistons 31, 32, 33, and 34 are placed in parallel in the X and Y directions intersecting with the Z direction, which is the longitudinal direction of the cylinder main body 50, within the cylinder main body 50.

In the first embodiment, as shown in FIGS. 4 and 5, the cylinder main body 50 includes a first cylinder 51, a second cylinder 52, a third cylinder 53, and a fourth cylinder 54 in which the pistons 31, 32, 33, and 34 are housed, respectively. A first fluid drive 62*a*, a second fluid drive 62*b*, a third fluid drive 62*c*, and a fourth fluid drive 62*d* are provided to perform at least one of injecting a fluid into the cylinders 51, 52, 53, and 54 to move the pistons 31, 32, 33, and 34, respectively, or suctioning the fluid from the cylinders 51, 52, 53, and 54 to move the pistons 31, 32, 33, and 34, respectively. The first fluid drive 62*a*, the second fluid drive 62*b*, the third fluid drive 62*c*, and the fourth fluid drive 62*d* inject the fluid into the cylinders 51, 52, 53, and 54 from the proximal end side through a first tube 61*a*, a second tube 61*b*, a third tube 61*c*, and a fourth tube 61*d* to move the pistons 31, 32, 33, and 34, respectively. The first fluid drive 62*a*, the second fluid drive 62*b*, the third fluid drive 62*c*, and the fourth fluid drive 62*d* may suction the fluid, or may perform both injection and suction. Furthermore, the fluid drives 62*a*, 62*b*, 62*c*, and 62*d* may inject the fluid into both the proximal end sides and the distal end sides of the cylinders 51, 52, 53, and 54, respectively. Thus, the pistons 31, 32, 33, and 34 are moved both toward the proximal end and toward the distal end.

Holes 50*a*, 50*b*, 50*c*, and 50*d* are provided on the proximal end sides of the cylinders 51, 52, 53, and 54, into which the first tube 61*a*, the second tube 61*b*, the third tube 61*c*, and the fourth tube 61*d* are inserted, respectively. Furthermore, the fluid for moving the pistons 31, 32, 33, and 34 is white oil, physiological saline, or air, for example.

As shown in FIG. 3, the fluid drives 62*a*, 62*b*, 62*c*, and 62*d* each include a cylinder piston, for example. The fluid drives 62*a*, 62*b*, 62*c*, and 62*d* are driven independently of each other. The fluid drives 62*a*, 62*b*, 62*c*, and 62*d* are driven by a controller 63. For example, when a user operates an operation unit 64*a* of a remote control apparatus 64, operation commands for rotation of the first jaw 11 and the second jaw 12, for example, are input to the controller 63. The controller 63 controls the operation of each of the fluid drives 62*a*, 62*b*, 62*c*, and 62*d* based on the operation commands. Thus, the surgical medical instrument 100 is operated according to the operation of the user.

Figure 7:
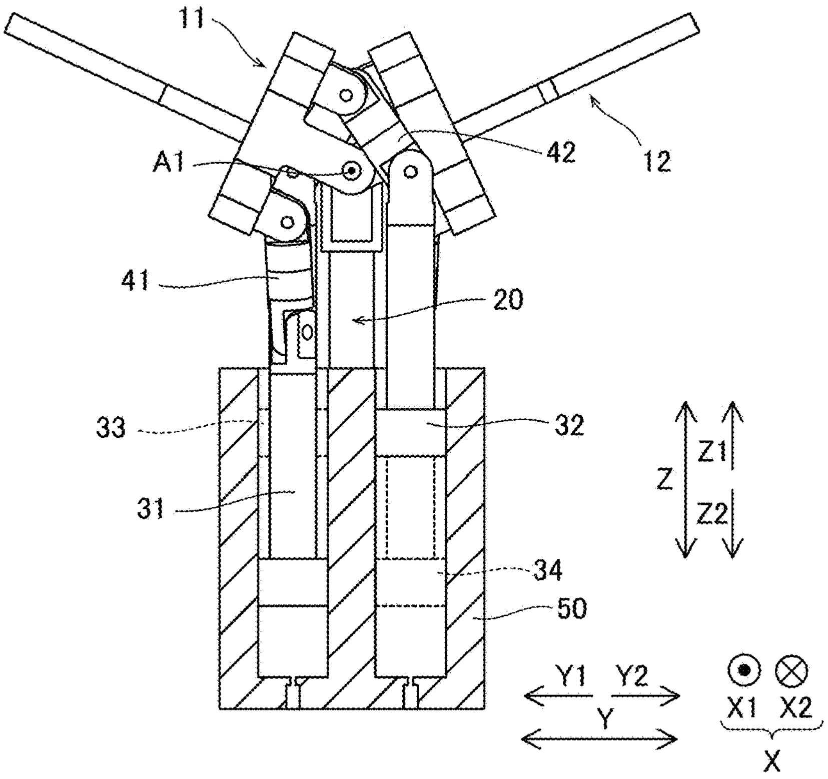
FIG. 7 is a diagram showing a state in which a first jaw and a second jaw of the surgical medical instrument are rotated about a jaw rotation axis.

In the first embodiment, as shown in FIG. 7, the first jaw 11 is rotated about the jaw rotation axis A1 by the first piston 31 and the second piston 32, and the second jaw 12 is rotated about the jaw rotation axis A1 by the third piston 33 and the fourth piston 34. Specifically, when at least one of the first piston 31 and the second piston 32 is moved, the other is moved in the opposite direction, and the first jaw 11 is rotated. Moreover, when at least one of the third piston 33 and the fourth piston 34 is moved, the other is moved in the opposite direction, and the second jaw 12 is rotated.

Figure 8:
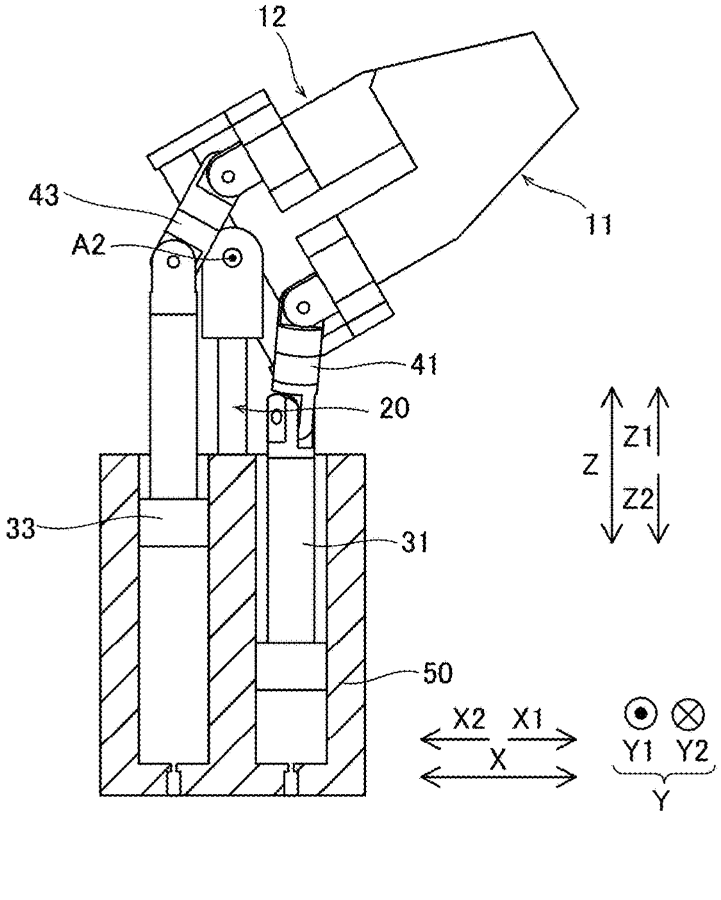
FIG. 8 is a diagram showing a state in which the first jaw and the second jaw of the surgical medical instrument are rotated about a wrist rotation axis.

In the first embodiment, as shown in FIG. 8, the first jaw 11 and the second jaw 12 are rotated about the wrist rotation axis A2 by the first piston 31, the second piston 32, the third piston 33, and the fourth piston 34. The first jaw 11 and the second jaw 12 are rotated to one side about the wrist rotation axis A2 by moving the first piston 31 and the second piston 32 toward the distal end. The first jaw 11 and the second jaw 12 are rotated to the other side about the wrist rotation axis A2 by moving the third piston 33 and the fourth piston 34 toward the distal end.

Advantages of First Embodiment

The first jaw 11 and the second jaw 12 are operable to be rotated about the jaw rotation axis A1 and about the wrist rotation axis A2 by the four pistons 31, 32, 33, and 34. Furthermore, the four pistons 31, 32, 33, and 34 are placed in parallel in the directions intersecting with the Z direction. Accordingly, as compared with a case in which pistons for rotating the first jaw 11 and the second jaw 12 about the jaw rotation axis A1 and pistons for rotating the first jaw 11 and the second jaw 12 about the wrist rotation axis A2 are placed separately, and the pistons for rotating the first jaw 11 and the second jaw 12 about the jaw rotation axis A1 and the pistons for rotating the first jaw 11 and the second jaw 12 about the wrist rotation axis A2 are placed in series along the Z direction, the length of the surgical medical instrument 100 can be reduced. Therefore, when the surgical medical instrument 100 curves or bends to pass around an obstacle within the body of a patient, the surgical medical instrument 100 can easily enter a narrow space. Furthermore, the surgical medical instrument 100 can easily enter a narrow space, and thus it is possible to easily perform work with the surgical medical instrument 100 entering a narrow space.

Each of the links 41, 42, 43, and 44 includes a plurality of rotational joints. Accordingly, the rotational degrees of freedom of each of the links 41, 42, 43, and 44 are increased, and thus the rotatable angles of the first jaw 11 and the second jaw 12 about the jaw rotation axis A1 and about the wrist rotation axis A2 can be increased.

The links 41, 42, 43, and 44 each has five rotational degrees of freedom. Thus, each of the links 41, 42, 43, and 44 has five rotational degrees of freedom, and thus the rotatable angles of the first jaw 11 and the second jaw 12 can be increased.

The first jaw 11 is rotated about the jaw rotation axis A1 by the first piston 31 and the second piston 32, and the second jaw 12 is rotated about the jaw rotation axis A1 by the third piston 33 and the fourth piston 34. Moreover, the first jaw 11 and the second jaw 12 are rotated about the wrist rotation axis A2 by the first piston 31, the second piston 32, the third piston 33, and the fourth piston 34. Accordingly, the number of pistons can be reduced as compared with a case in which pistons are placed separately for rotation about the jaw rotation axis A1 and rotation about the wrist rotation axis A2.

The shaft 13 is operable to support the first jaw 11 and the second jaw 12, and has the jaw rotation axis A1 and the wrist rotation axis A2. Accordingly, a distance between the jaw rotation axis A1 and the wrist rotation axis A2 is reduced, and thus the operability of the surgical medical instrument 100 can be improved.

The shaft 13 is arranged between the distal end and the proximal end of each of the links 41, 42, 43, and 44 when the first jaw 11 and the second jaw 12 are arranged along the Z direction. Accordingly, the length of the surgical medical instrument 100 can be reduced as compared with a case in which the shaft 13 is arranged closer to the proximal end than each of the links 41, 42, 43, and 44.

The pistons 31, 32, 33, and 34 are placed in parallel in the directions intersecting with the longitudinal direction of the cylinder main body 50, within the cylinder main body 50. Accordingly, the pistons 31, 32, 33, and 34 are placed adjacent to each other within the cylinder main body 50, and thus an increase in the length of the cylinder main body 50 can be reduced or prevented.

The surgical medical instrument 100 includes the fluid drives 62*a*, 62*b*, 62*c*, and 62*d* to inject the fluid to move the pistons 31, 32, 33, and 34 housed in the cylinders 51, 52, 53, and 54, respectively. Accordingly, the fluid can be easily injected into the cylinders 51, 52, 53, and 54 by the fluid drives 62*a*, 62*b*, 62*c*, and 62*d*.

Second Embodiment

Figure 9:
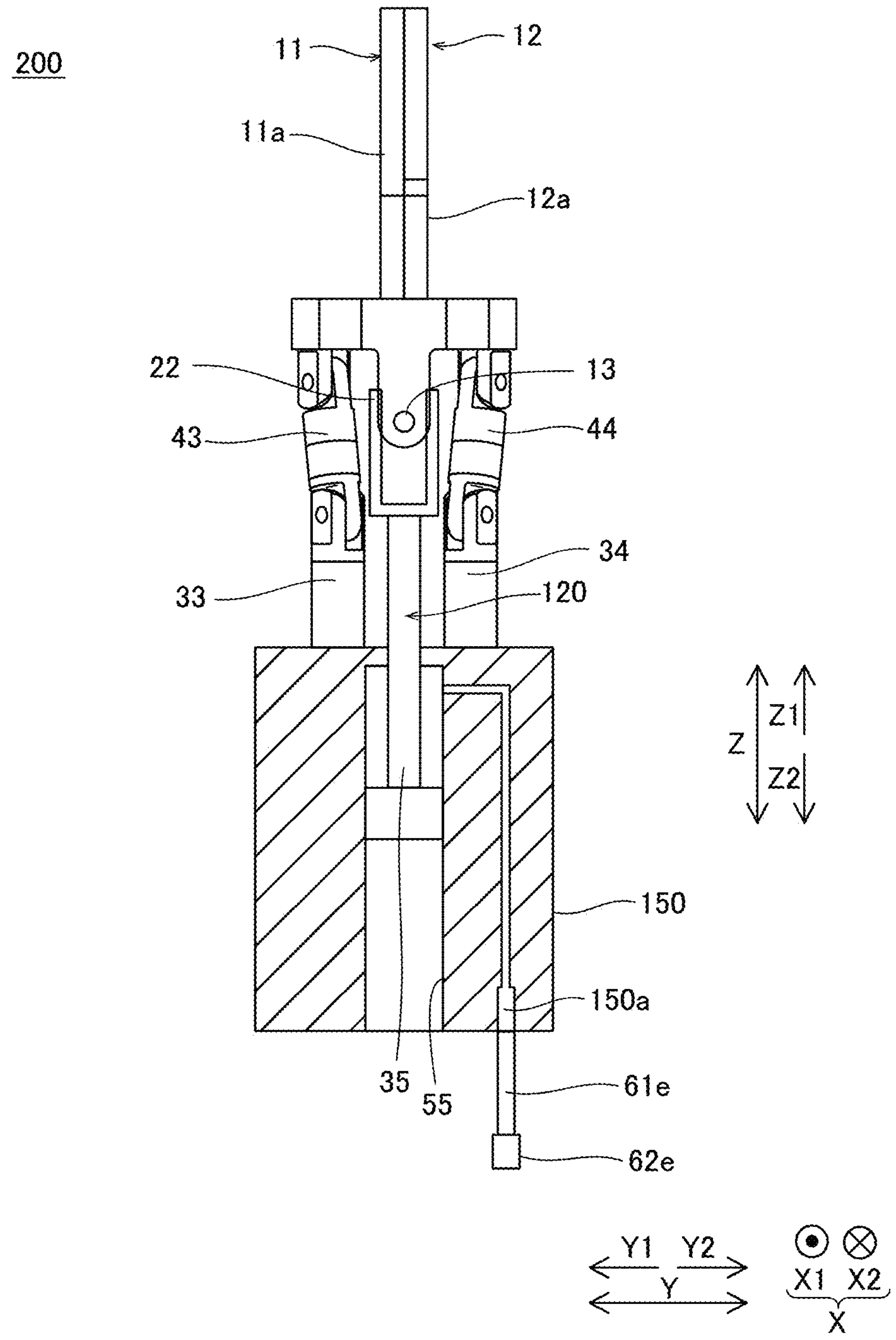
FIG. 9 is a sectional view showing a fifth piston of a surgical medical instrument according to a second embodiment, as viewed from an X1 side.

A surgical medical instrument 200 according to a second embodiment is now described. As shown in FIG. 9, the surgical medical instrument 200 includes a fifth piston 35 to move a support 120 along a Z direction. Specifically, in the surgical medical instrument 200, the support 120 and the fifth piston 35 are integral and unitary with each other. A fifth cylinder 55 in which the fifth piston 35 is housed is placed in a central portion of a cylinder main body 150. Pistons 31, 32, 33, 34, and 35 are placed in parallel in a direction intersecting with the Z direction.

The surgical medical instrument 200 includes a fifth fluid drive 62*e* to perform at least one of injecting a fluid into the cylinder 55 to move the piston 35 or suctioning the fluid from the cylinder 55 to move the piston 35. The fifth fluid drive 62*e* injects the fluid into the fifth cylinder 55 through a tube 61*e*. The fifth cylinder 55 includes a hole 150*a* into which the tube 61*e* is inserted. The fluid is supplied to the cylinder 55 from the distal end side. The fluid for moving the fifth piston 35 is white oil, physiological saline, or air, for example.

Figure 10:
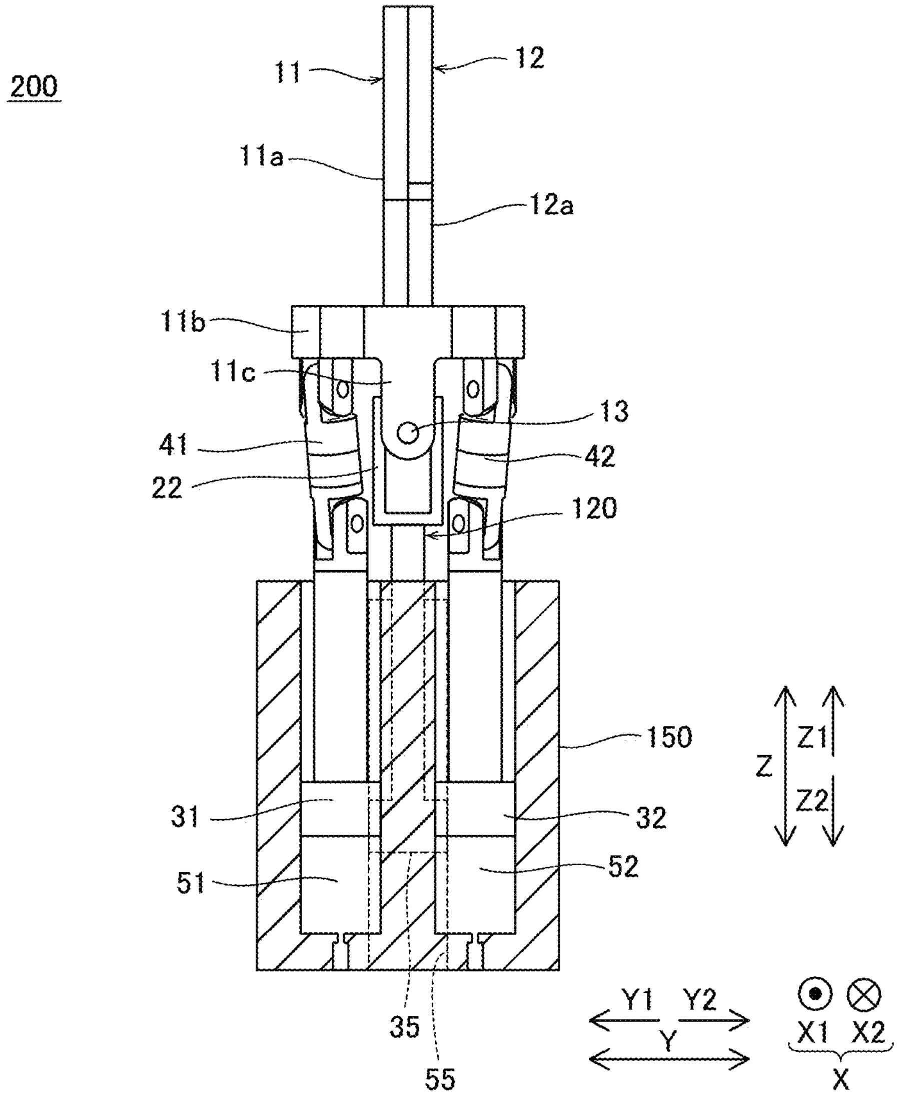
FIG. 10 is a sectional view showing a first piston and a second piston of the surgical medical instrument according to the second embodiment, as viewed from the X1 side.
Figure 11:
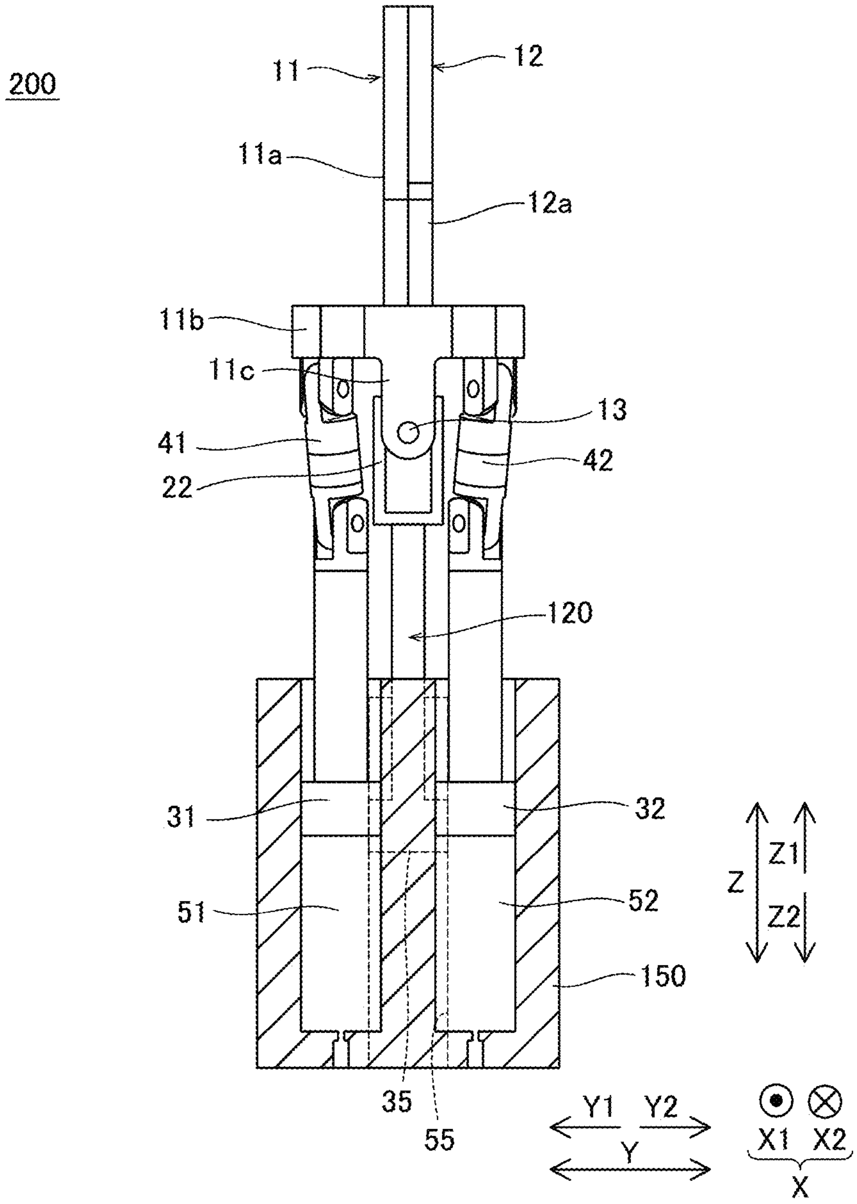
FIG. 11 is a diagram showing the surgical medical instrument according to the second embodiment in an extended state.
Figure 12:
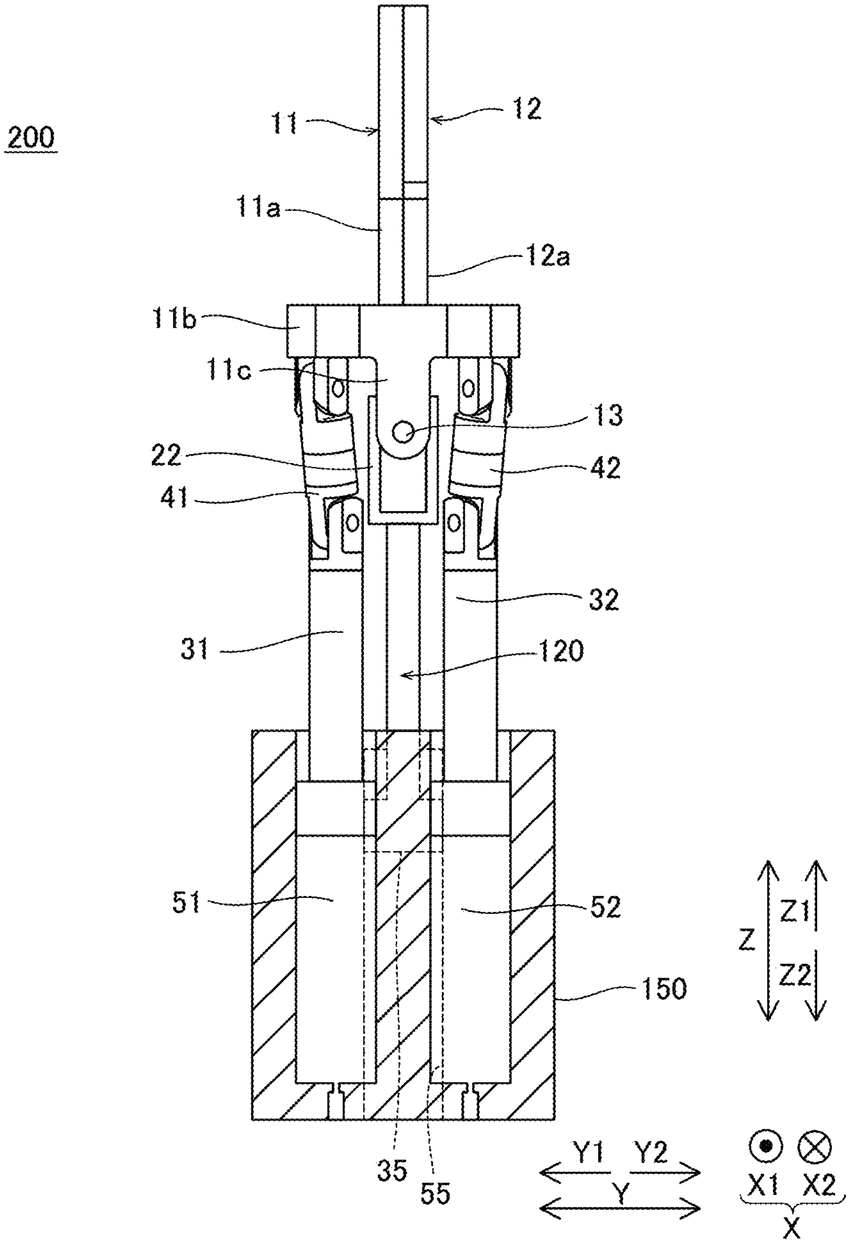
FIG. 12 is a diagram showing the surgical medical instrument according to the second embodiment in a further extended state.

As shown in FIGS. 10, 11, and 12, the pistons 31, 32, 33, 34, and 35 are moved from the proximal end side to the distal end side by injecting the fluid from fluid drives 62*a*, 62*b*, 62*c*, and 62*d* into the proximal end sides of the cylinders 51, 52, 53, and 54, respectively. Thus, a first jaw 11 and a second jaw 12 are moved toward the distal end. Furthermore, the pistons 31, 32, 33, 34, and 35 are moved from the distal end side to the proximal end side by injecting the fluid from the fifth fluid drive 62*e* into the distal end side of the cylinder 55. Thus, the first jaw 11 and the second jaw 12 are moved toward the proximal end.

The fluid drives 62*a*, 62*b*, 62*c*, 62*d*, and 62*e* may perform both injection and suction of the fluid. The fluid drives 62*a*, 62*b*, 62*c*, 62*d*, and 62*e* may inject the fluid into both proximal ends and distal ends of the cylinders 51, 52, 53, 54, and 55, respectively. Thus, the pistons 31, 32, 33, 34, and 35 are moved both toward the proximal end and toward the distal end.

Advantages of Second Embodiment

The surgical medical instrument 200 includes the fifth piston 35 to move the support 120 along the Z direction, and the fifth fluid drive 62*e* to inject the fluid into the fifth cylinder 55 to move the fifth piston 35. Accordingly, the surgical medical instrument 200 can be expanded or contracted in length.

Third Embodiment

Figure 13:
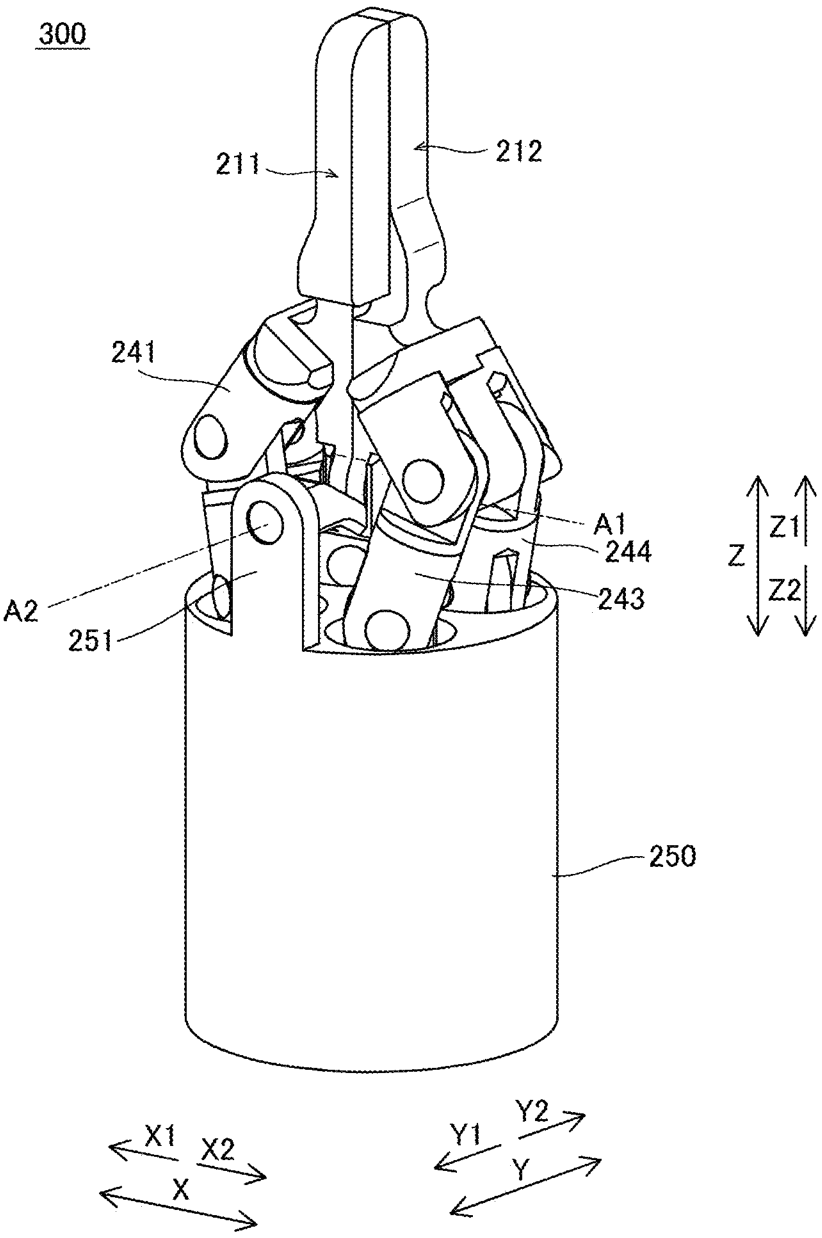
FIG. 13 is a perspective view of a surgical medical instrument according to a third embodiment.
Figure 14:
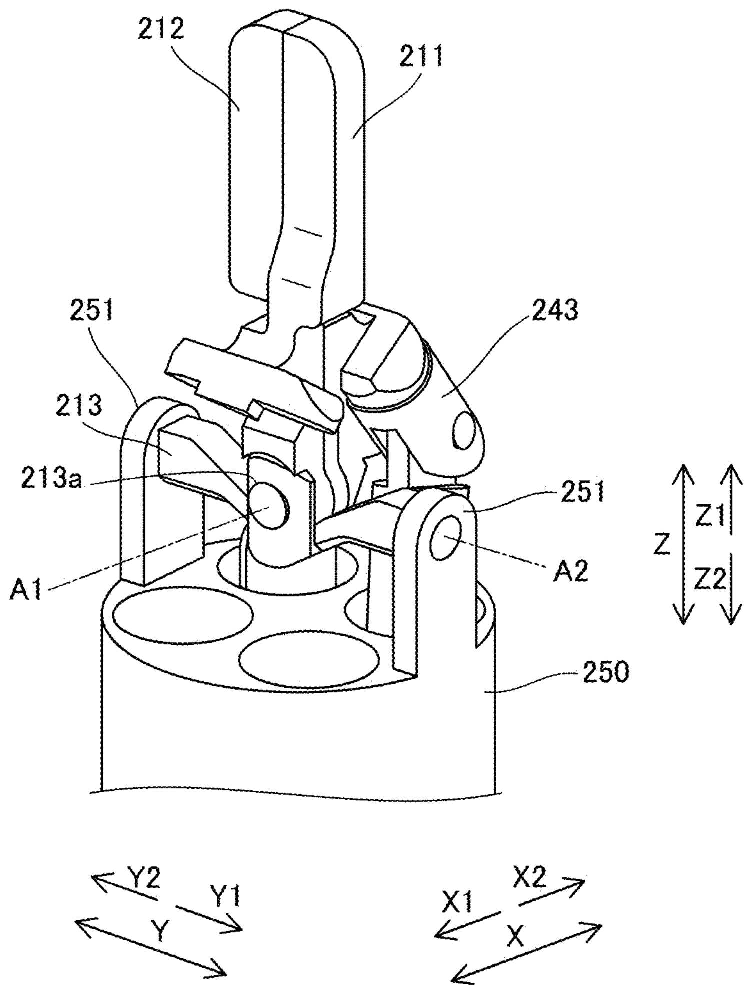
FIG. 14 is a perspective view showing a shaft of the surgical medical instrument according to the third embodiment.

A surgical medical instrument 300 according to a third embodiment is now described. As shown in FIGS. 13, 14, 15, and 16, the surgical medical instrument 300 includes a first jaw 211, a second jaw 212, a shaft 213, a first link 241, a second link 242, a third link 243, and a fourth link 244. In FIG. 14, illustration of the first link 241 and the second link 242 are omitted.

Figure 15:
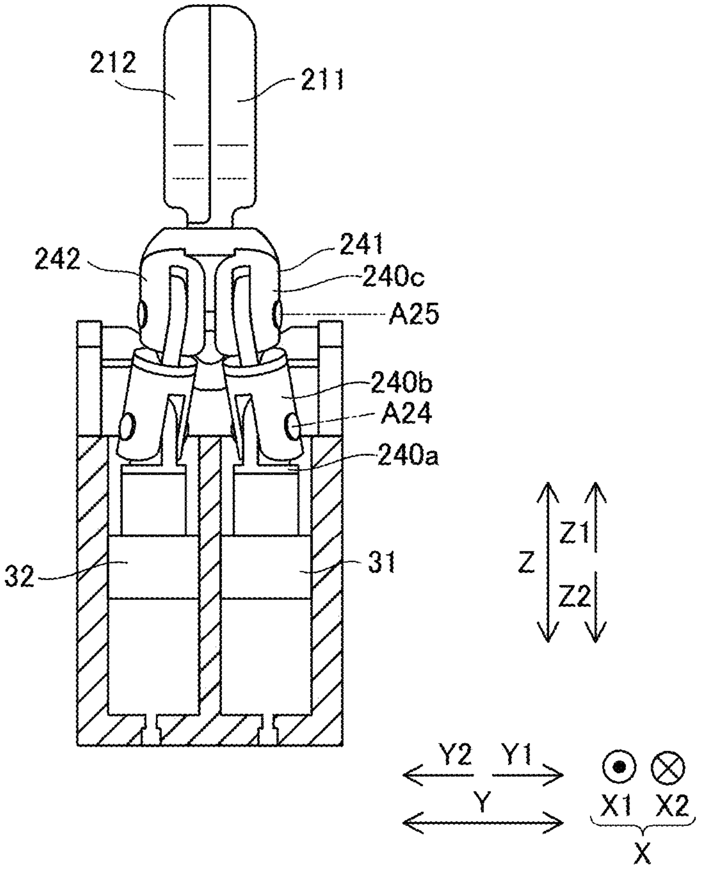
FIG. 15 is a sectional view of the surgical medical instrument according to the third embodiment, as viewed from an X1 side.
Figure 16:
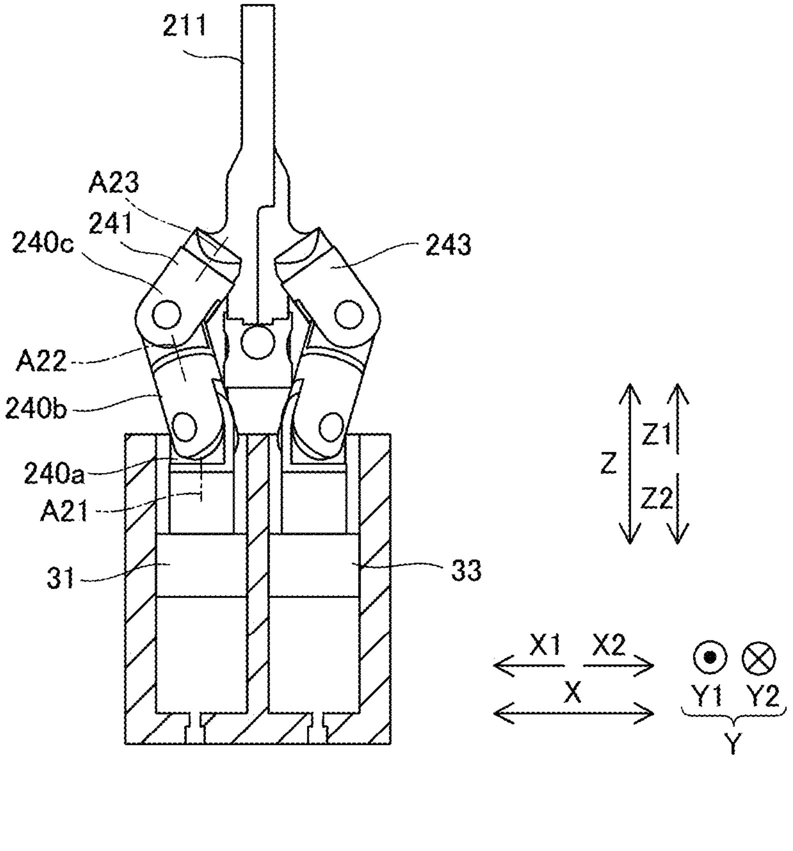
FIG. 16 is a sectional view of the surgical medical instrument according to the third embodiment, as viewed from a Y1 side.

As shown in FIG. 14, the shaft 213 supports the first jaw 211 and the second jaw 212, and has a jaw rotation axis A1 and a wrist rotation axis A2. A pin member 213*a* passes through the shaft 213. The pin member 213*a* is inserted into a portion of each of the first jaw 211 and the second jaw 212 on the proximal end side. Both ends of the shaft 213 are supported by supports 251 of a cylinder main body 250. As shown in FIG. 15, the first link 241 and the second link 242 are connected to the first jaw 211. As shown in FIG. 13, the third link 243 and the fourth link 244 are connected to the second jaw 212. As shown in FIGS. 15 and 16, pistons 31, 32, 33, and 34 are connected to the links 241, 242, 243, and 244, respectively, similarly to the first embodiment. The links 241, 242, 243, and 244 each include a first portion 240*a*, a second portion 240*c*, and a third portion 240*b*. The first portion 240*a* rotates about an axis A21, the second portion 240*c* rotates about an axis A23, and the third portion 240*b* rotates about an axis A22. The first portion 240*a* and the third portion 240*b* are bent about an axis A24. The third portion 240*b* and the second portion 240*c* are bent about an axis A25.

In the third embodiment, as shown in FIGS. 15 and 16, the second portion 240*c* and the third portion 240*b* are arranged in a skew positional relationship with each other when the first jaw 211 and the second jaw 212 are arranged along the Z direction. When the first jaw 211 and the second jaw 212 are arranged along the Z direction, the second portion 240*c* and the third portion 240*b* are arranged in a bent manner. Furthermore, the first portion 240*a* is arranged along the Z direction. When the first jaw 211 and the second jaw 212 are arranged along the Z direction, the first portion 240*a* and the third portion 240*b* are arranged in a bent manner.

When two of the axis A21 about which the first portion 240*a* rotates, the axis A23 about which the second portion 240*c* rotates, and the axis A22 about which the third portion 240*b* rotates are arranged on a straight line, the link may not be able to bend or rotate even when the link is pressed toward the distal end by the piston. In other words, a singularity exists. Therefore, the first portion 240*a*, the second portion 240*c*, and the third portion 240*b* are arranged as described above such that it is possible to prevent a singularity from occurring in a rotation range of the first jaw 211 and the second jaw 212.

Advantages of Third Embodiment

The second portion 240*c* and the third portion 240*b* intersect with the Z direction when the first jaw 211 and the second jaw 212 are arranged along the Z direction. Accordingly, even when the link is pressed toward the distal end by the piston, it is possible to prevent a singularity at which the link cannot be bent or rotated from occurring in the rotation range of the first jaw 211 and the second jaw 212.

Modified Examples

The embodiments disclosed this time must be considered as illustrative in all points and not restrictive. The scope of the present disclosure is not shown by the above description of the embodiments but by the scope of claims for patent, and all modifications (modified examples) within the meaning and scope equivalent to the scope of claims for patent are further included.

For example, while the example in which each of the links has a hinge structure and a swivel structure has been shown in each of the first, second, and third embodiments, the present disclosure is not limited to this. For example, each of the links may be a universal joint or a spherical joint.

While the example in which each of the links has five rotational degrees of freedom has been shown in each of the first, second, and third embodiments, the present disclosure is not limited to this. For example, the number of rotational degrees of freedom of each link may be other than five.

Figure 17:
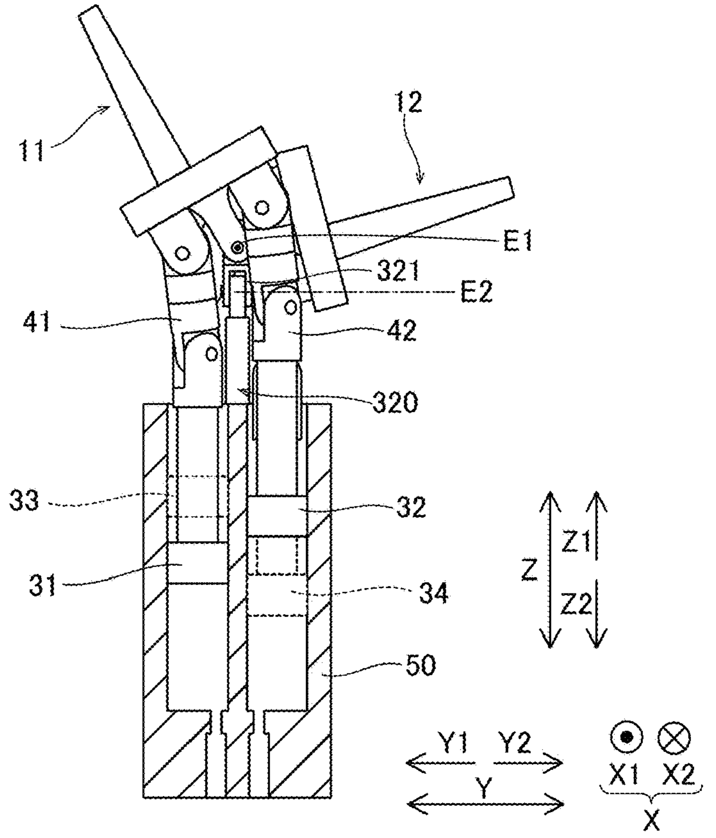
FIG. 17 is a diagram showing a state in which a first jaw and a second jaw of a surgical medical instrument according to a modified example are rotated about a jaw rotation axis.
Figure 18:
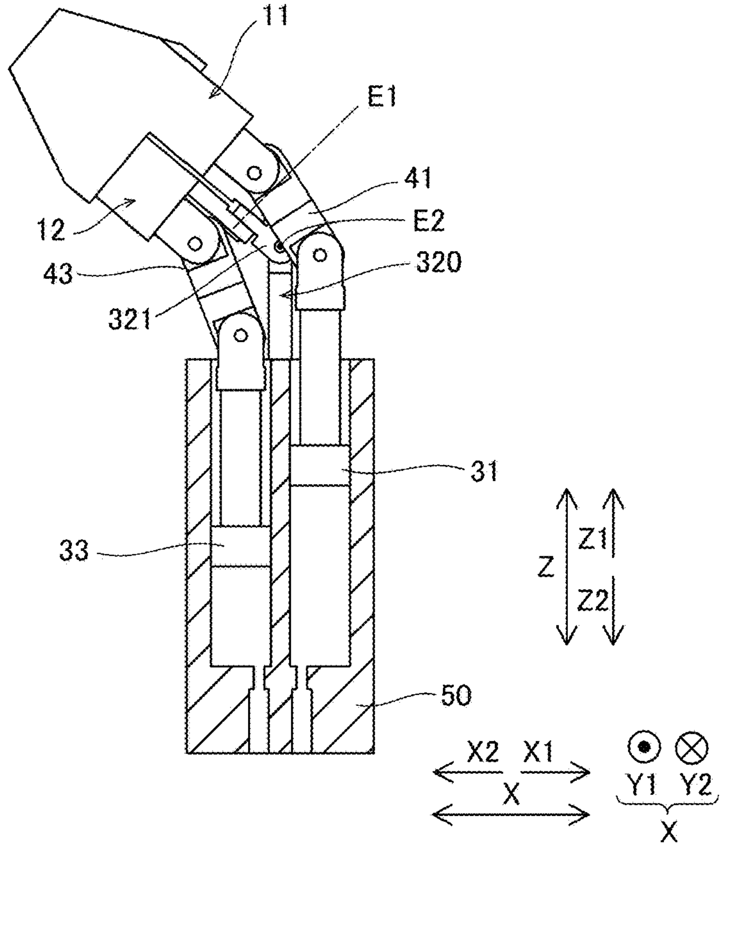
FIG. 18 is a diagram showing a state in which the first jaw and the second jaw of the surgical medical instrument according to the modified example are rotated about a wrist rotation axis.

While the example in which the shaft 13 is columnar has been shown in each of the first and second embodiments, the present disclosure is not limited to this. As shown in FIGS. 17 and 18, a U-shaped member 321 is attached to a distal end of a support 320. The member 321 rotates with respect to the support 320. An axis about which the member 321 rotates with respect to the support 320 is a wrist rotation axis E2. A distal end of the member 321 has a flat plate shape. A first jaw 11 and a second jaw 12 are attached to the distal end of the member 321. The first jaw 11 and the second jaw 12 rotate with respect to the distal end of the member 321. An axis about which the first jaw 11 and the second jaw 12 rotate with respect to the distal end side of the member 321 is a jaw rotation axis E1 of the first jaw 11 and the second jaw 12.

The present disclosure may also be practiced not only as a surgical medical instrument, but in various forms. For example, the present disclosure may be practiced in the form of a gripping device for construction machinery such as a crusher, a hand for an industrial robot, etc. In such a from, the surgical medical instruments 100, 200, and 300 in the above embodiments correspond to the gripping device. Furthermore, the first jaws 11 and 211 correspond to a first gripper, and the second jaws 12 and 212 correspond to a second gripper.

Aspects

It will be appreciated by those skilled in the art that the exemplary embodiments described above are specific examples of the following aspects.

(Item 1)

A surgical medical instrument comprising:
- a first jaw;
- a second jaw;
- a first piston and a second piston to rotate the first jaw;
- a third piston and a fourth piston to rotate the second jaw;
- a first link to connect the first jaw to the first piston;
- a second link to connect the first jaw to the second piston;
- a third link to connect the second jaw to the third piston; and
- a fourth link to connect the second jaw to the fourth piston; wherein
- the first to fourth pistons are placed in parallel in a direction intersecting with a longitudinal direction of the surgical medical instrument; and the first jaw and the second jaw are operable to be rotated about a jaw rotation axis and about a wrist rotation axis by the first to fourth pistons.

(Item 2)

The surgical medical instrument according to item 1, wherein each of the first to fourth links includes a plurality of rotational joints.

(Item 3)

The surgical medical instrument according to item 2, wherein each of the first to fourth links includes a first portion on a proximal end side, a second portion on a distal end side, and a third portion between the first portion and the second portion.

(Item 4)

The surgical medical instrument according to item 3, wherein
- a portion in which the first portion is connected to the third portion has a hinge structure;
- a portion in which the third portion is connected to the second portion has a hinge structure; and
- each of the first portion, the second portion, and the third portion has a swivel structure such that each of the first to fourth links has five rotational degrees of freedom.

(Item 5)

The surgical medical instrument according to item 3 or 4, wherein the second portion and the third portion are arranged in a skew positional relationship with each other when the first jaw and the second jaw are arranged along the longitudinal direction of the surgical medical instrument.

(Item 6)

The surgical medical instrument according to any one of items 1 to 5, wherein
- the first jaw is operable to be rotated about the jaw rotation axis by the first piston and the second piston; and
- the second jaw is operable to be rotated about the jaw rotation axis by the third piston and the fourth piston.

(Item 7)

The surgical medical instrument according to any one of items 1 to 6, wherein the first jaw and the second jaw are operable to be rotated about the wrist rotation axis by the first piston, the second piston, the third piston, and the fourth piston.

(Item 8)

The surgical medical instrument according to any one of items 1 to 7, further comprising:

a shaft to support the first jaw and the second jaw, and having the jaw rotation axis and the wrist rotation axis.

(Item 9)

The surgical medical instrument according to item 8, wherein the shaft is arranged between a distal end and a proximal end of each of the first to fourth links when the first jaw and the second jaw are arranged along the longitudinal direction of the surgical medical instrument.

(Item 10)

The surgical medical instrument according to any one of items 1 to 9, further comprising:

a cylinder main body in which the first to fourth pistons are housed; wherein the first to fourth pistons are placed in parallel in the direction intersecting with the longitudinal direction of the surgical medical instrument, within the cylinder main body.

(Item 11)

The surgical medical instrument according to item 10, wherein the cylinder main body includes a first cylinder, a second cylinder, a third cylinder, and a fourth cylinder in which the first piston, the second piston, the third piston, and the fourth piston are housed, respectively; and the surgical medical instrument further comprises a first fluid drive, a second fluid drive, a third fluid drive, and a fourth fluid drive to perform at least one of injecting a fluid into the first to fourth cylinders to move the first to fourth pistons, respectively, or suctioning the fluid from the first to fourth cylinders to move the first to fourth pistons, respectively.

(Item 12)

The surgical medical instrument according to any one of items 1 to 11, further comprising:

a shaft to support the first jaw and the second jaw, and having the jaw rotation axis and the wrist rotation axis;

a support to support the shaft; and a fifth piston to move the support along the longitudinal direction of the surgical medical instrument.

(Item 13)

The surgical medical instrument according to item 12, further comprising:

a cylinder main body in which the first to fifth pistons are housed; wherein the cylinder main body includes a first cylinder, a second cylinder, a third cylinder, a fourth cylinder, and a fifth cylinder in which the first piston, the second piston, the third piston, the fourth piston, and the fifth piston are housed, respectively; and the surgical medical instrument further comprises a first fluid drive, a second fluid drive, a third fluid drive, a fourth fluid drive, and a fifth fluid drive to perform at least one of injecting a fluid into the first to fifth cylinders to move the first to fifth pistons, respectively, or suctioning the fluid from the first to fifth cylinders to move the first to fifth pistons, respectively.

(Item 14)

A gripping device comprising:

a first gripper;

a second gripper;

a first piston and a second piston to rotate the first gripper;

a third piston and a fourth piston to rotate the second gripper;

a first link to connect the first gripper to the first piston;

a second link to connect the first gripper to the second piston;

a third link to connect the second gripper to the third piston; and a fourth link to connect the second gripper to the fourth piston; wherein the first to fourth pistons are placed in parallel in a direction intersecting with a longitudinal direction of the gripping device; and the first gripper and the second gripper are operable to be rotated about a gripper rotation axis and about a wrist rotation axis by the first to fourth pistons.

The invention claimed is:

1. A surgical medical instrument comprising:

a first jaw;

a second jaw;

a first piston and a second piston to rotate the first jaw;

a third piston and a fourth piston to rotate the second jaw;

a first link to connect the first jaw to the first piston;

a second link to connect the first jaw to the second piston;

a third link to connect the second jaw to the third piston; and a fourth link to connect the second jaw to the fourth piston; wherein the first to fourth pistons are placed in parallel in a direction intersecting with a longitudinal direction of the surgical medical instrument; and the first jaw and the second jaw are operable to be rotated both about a jaw rotation axis and about a wrist rotation axis by the first to fourth pistons.

2. The surgical medical instrument according to claim 1, wherein each of the first to fourth links includes a plurality of rotational joints.

3. The surgical medical instrument according to claim 2, wherein each of the first to fourth links includes a first portion on a proximal end side, a second portion on a distal end side, and a third portion between the first portion and the second portion.

4. The surgical medical instrument according to claim 3, wherein a portion in which the first portion is connected to the third portion has a hinge structure;

a portion in which the third portion is connected to the second portion has a hinge structure; and each of the first portion, the second portion, and the third portion has a swivel structure such that each of the first to fourth links has five rotational degrees of freedom.

5. The surgical medical instrument according to claim 3, wherein the second portion and the third portion are arranged in a skew positional relationship with each other when the first jaw and the second jaw are arranged along the longitudinal direction of the surgical medical instrument.

6. The surgical medical instrument according to claim 1, wherein the first jaw is operable to be rotated about the jaw rotation axis by the first piston and the second piston; and the second jaw is operable to be rotated about the jaw rotation axis by the third piston and the fourth piston.

7. The surgical medical instrument according to claim 1, wherein the first jaw and the second jaw are operable to be rotated about the wrist rotation axis by the first piston, the second piston, the third piston, and the fourth piston.

8. The surgical medical instrument according to claim 1, further comprising:

a shaft to support the first jaw and the second jaw, and having the jaw rotation axis and the wrist rotation axis.

9. The surgical medical instrument according to claim 8, wherein the shaft is arranged between a distal end and a proximal end of each of the first to fourth links when the first jaw and the second jaw are arranged along the longitudinal direction of the surgical medical instrument.

10. The surgical medical instrument according to claim 1, further comprising:

a cylinder main body in which the first to fourth pistons are housed; wherein the first to fourth pistons are placed in parallel in the direction intersecting with the longitudinal direction of the surgical medical instrument, within the cylinder main body.

11. The surgical medical instrument according to claim 10, wherein the cylinder main body includes a first cylinder, a second cylinder, a third cylinder, and a fourth cylinder in which the first piston, the second piston, the third piston, and the fourth piston are housed, respectively; and the surgical medical instrument further comprises a first fluid drive, a second fluid drive, a third fluid drive, and a fourth fluid drive to perform at least one of injecting a fluid into the first to fourth cylinders to move the first to fourth pistons, respectively, or suctioning the fluid from the first to fourth cylinders to move the first to fourth pistons, respectively.

12. The surgical medical instrument according to claim 1, further comprising:

a shaft to support the first jaw and the second jaw, and having the jaw rotation axis and the wrist rotation axis;

a support to support the shaft; and a fifth piston to move the support along the longitudinal direction of the surgical medical instrument.

13. The surgical medical instrument according to claim 12, further comprising:

a cylinder main body in which the first to fifth pistons are housed; wherein the cylinder main body includes a first cylinder, a second cylinder, a third cylinder, a fourth cylinder, and a fifth cylinder in which the first piston, the second piston, the third piston, the fourth piston, and the fifth piston are housed, respectively; and the surgical medical instrument further comprises a first fluid drive, a second fluid drive, a third fluid drive, a fourth fluid drive, and a fifth fluid drive to perform at least one of injecting a fluid into the first to fifth cylinders to move the first to fifth pistons, respectively, or suctioning the fluid from the first to fifth cylinders to move the first to fifth pistons, respectively.

14. The surgical medical instrument according to claim 1, wherein the first to fourth pistons are placed at a substantially same position in the longitudinal direction of the surgical medical instrument.

15. A gripping device comprising:

a first gripper;

a second gripper;

a first piston and a second piston to rotate the first gripper;

a third piston and a fourth piston to rotate the second gripper;

a first link to connect the first gripper to the first piston;

a second link to connect the first gripper to the second piston;

a third link to connect the second gripper to the third piston; and a fourth link to connect the second gripper to the fourth piston; wherein the first to fourth pistons are placed in parallel in a direction intersecting with a longitudinal direction of the gripping device; and the first gripper and the second gripper are operable to be rotated both about a gripper rotation axis and about a wrist rotation axis by the first to fourth pistons.

* * * * *